(12) United States Patent
Witowski

(10) Patent No.: US 7,846,136 B2
(45) Date of Patent: Dec. 7, 2010

(54) GRIPPING EDGE FOR A SYRINGE WITH IMPROVED PROTECTION AGAINST BURSTING

(75) Inventor: Norbert Witowski, Wolfenbüttel (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 526 days.

(21) Appl. No.: 11/512,414

(22) Filed: Aug. 30, 2006

(65) Prior Publication Data

US 2007/0088284 A1 Apr. 19, 2007

Related U.S. Application Data

(60) Provisional application No. 60/713,758, filed on Sep. 6, 2005.

(30) Foreign Application Priority Data

Aug. 31, 2005 (DE) .................. 10 2005 042 076

(51) Int. Cl.
*A61M 5/315* (2006.01)
(52) U.S. Cl. .................. 604/218; 604/187; 604/227
(58) Field of Classification Search .................. 604/187, 604/220, 221, 227, 232, 235
See application file for complete search history.

(56) References Cited

U.S. PATENT DOCUMENTS 5,897,532 A * 4/1999 Spallek et al. .............. 604/187

6,616,639 B2 * 9/2003 Gagnieux et al. .......... 604/192

FOREIGN PATENT DOCUMENTS

| DE | 197 23 851 C1 | 10/1998 |
|---|---|---|
| EP | 0723784 A1 | 7/1996 |
| FR | 2858931 A | 2/2005 |

* cited by examiner

*Primary Examiner*—Kevin C Sirmons
*Assistant Examiner*—Phillip Gray
(74) *Attorney, Agent, or Firm*—Millen, White, Zelano & Branigan, P.C.

(57) ABSTRACT

The invention relates to a gripping edge (1) for a syringe with: a sleeve (7) with a first opening (9) for attachment to a barrel (2) of the syringe and a second opening (10). The gripping edge (1) comprises a flange (8) that is attached to the sleeve (7) at a distance from the first opening (9). A large number of catches (11), which project radially toward the inside from the inside wall (21) of the sleeve (7), are provided to engage in a groove attached to an outside surface of the barrel (2) or projections (13) and to fasten the sleeve (7) and, over this, the gripping edge (1) to the barrel (2), whereby a considerable number of openings, in particular a considerable number of lengthwise openings (14) and/or a considerable number of transverse openings (15), are cut out in the sleeve (7). As a result, a locking of the gripping edge (1) to the barrel (2) in the case of lower assembly forces is possible, by which a bursting tendency of the barrel (2), in particular during assembly, is considerably reduced.

23 Claims, 5 Drawing Sheets

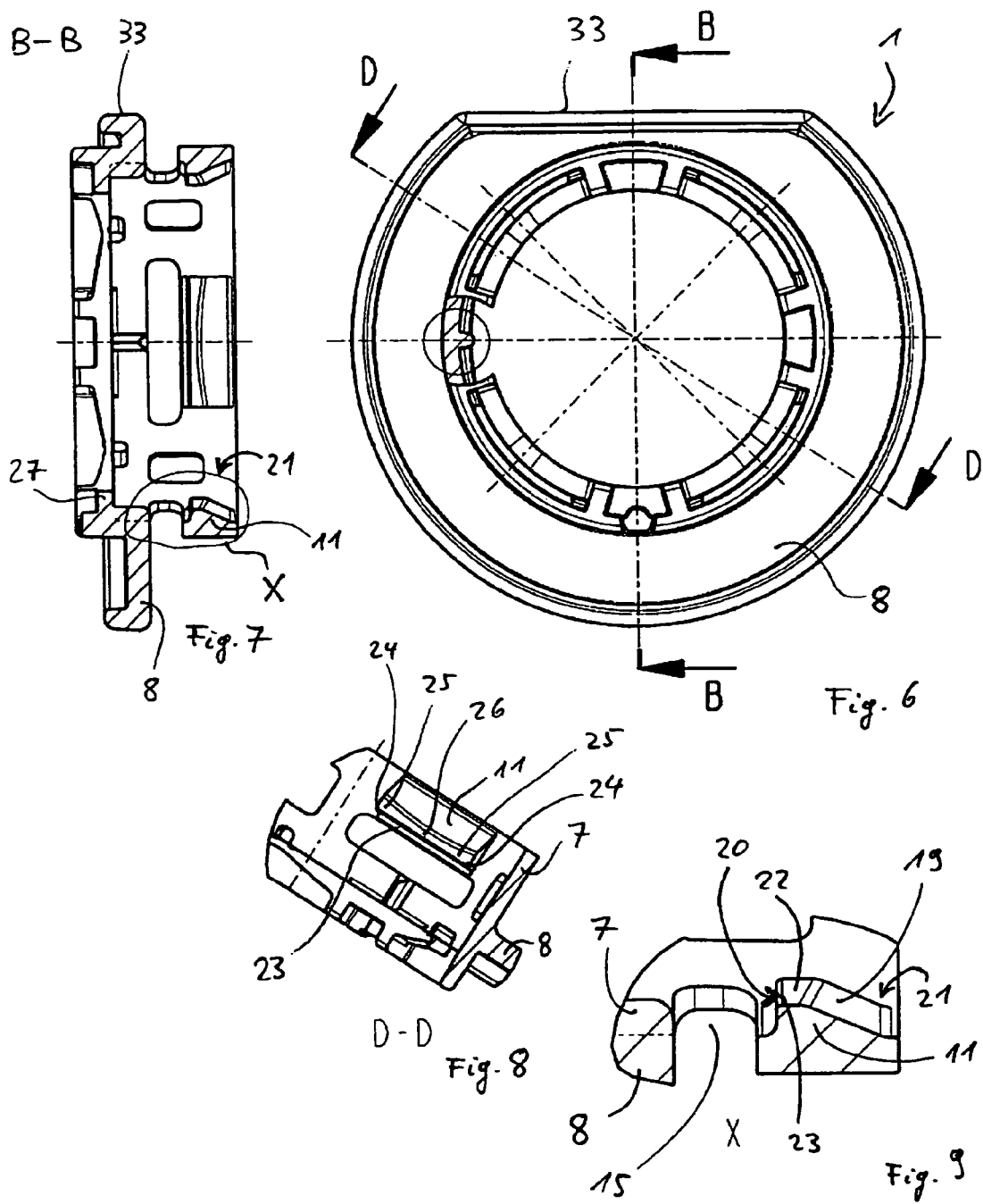

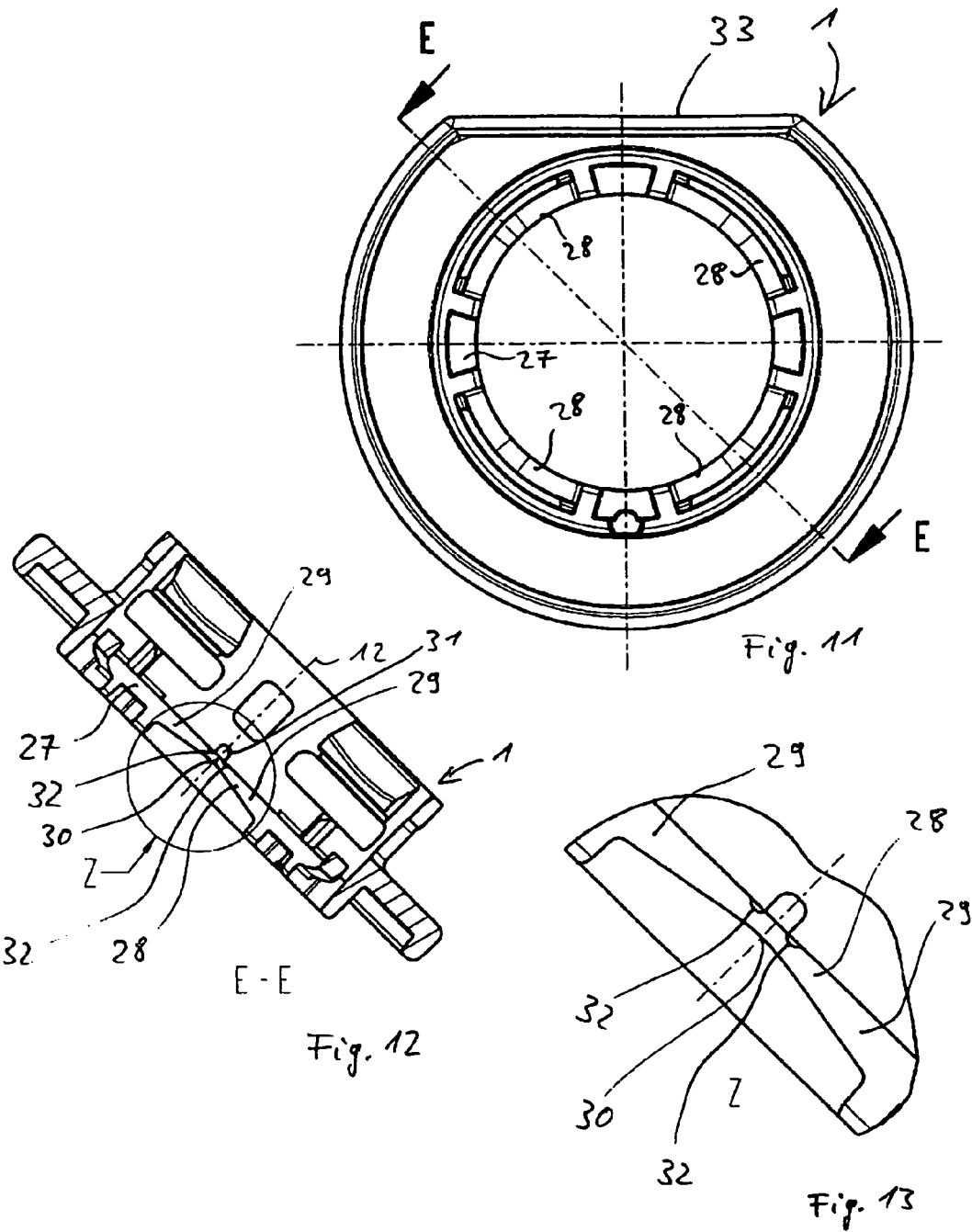

GRIPPING EDGE FOR A SYRINGE WITH IMPROVED PROTECTION AGAINST BURSTING

This application claims the benefit of the filing date of U.S. Provisional Application Ser. No. 60/713,758 filed Sep. 6, 2005.

This invention relates to a gripping edge for a syringe with an improved protection against bursting.

It is a general problem in syringes, which are composed of components, that the assembly of the components must be performed with high forces. The expenditure of these high forces results in the strength of the syringe being reduced. When using the syringe, especially when it is being used for a medium of high viscosity such as contrast media, or even during assembly, it can lead to destruction of the syringe and thus to risk for the patients or to an interruption of production sequences with economic losses.

As a solution for the aforementioned problem, it was proposed that an insert made of silicone polymer be installed in a receiving device for a barrel, which is formed on the gripping edge. The silicone polymer is, however, a very expensive insert, which leads to an increase in production costs of the syringe.

From EP 1 123 712 A, a barrel and a barrel holder are known. On its proximal end, i.e., on the end facing the user, the barrel has a flange that can be accommodated by a syringe holder. The flange that is molded onto the barrel increases the mechanical strength of the barrel.

A syringe that comprises a glass cartridge that is filled with a pharmaceutical liquid is known from EP 0 723 784 A1. The glass cartridge is made in a cylindrical shape and has a groove that goes around an outside surface on one end. Catches that project from a sleeve-like receiving of a gripping edge are engaged in the groove. The latter attach the gripping edge to the glass cartridge of the syringe.

The object of this invention is to provide an economical, improved gripping edge that reduces a syringe's tendency to burst. A gripping edge is required for a syringe that reduces the high assembly forces, ensures protection of the syringe against bursting even when mechanical injectors are used, and prevents twisting of the gripping edge, whereby the syringe is to be used for manual and high-speed application.

This object is achieved by a gripping edge according to claim 1. Preferred embodiments of the gripping edge are indicated in the subclaims.

In particular, a gripping edge for a syringe is attached to: a sleeve with a first opening for attachment to a barrel of the syringe and a second opening; a flange that is attached to the sleeve at a distance from the first opening; a large number of catches, which project radially toward the inside from the inside wall of the sleeve; whereby a considerable number of openings, in particular a considerable number of lengthwise openings and/or a considerable number of transverse openings, are cut out in the sleeve.

Such a gripping edge is used to protect the syringe during use, especially in the administration of a medium of high viscosity. The gripping edge is designed such that a tendency of the barrel to burst when the gripping edge is pressed is considerably reduced. The gripping edge is also used as a flange and as a connection between the barrel and an injector in which the syringe is to be used.

In particular, the openings, which are designed in particular as lengthwise openings and/or transverse openings, are used as expansion openings of the sleeve of the gripping edge. A pronounced reduction of the assembly force of the gripping edge on a barrel can be attributed to preferably four lengthwise and transverse openings.

The lengthwise openings and transverse openings are generally cut out as through-holes. The reduction of the assembly force can also be achieved by a configuration of the sleeve with a low wall strength. The lengthwise openings and transverse openings thus can also be designed so that a wall strength of the sleeve is only reduced in the cut-out lengthwise and/or transverse openings.

Openings that have a greater expansion in one axial direction of the sleeve than in a radial direction along one periphery of the sleeve are regarded as lengthwise openings. This is exactly the reverse in the case of transverse openings. The lengthwise openings and the tranverse openings are preferably designed as lengthwise hole-like slots or recesses. Otherwise formed or otherwise oriented openings can also be used, however.

To achieve an optimum deformation of the sleeve of the gripping edge during pressing, it is advantageous if the considerable number of openings, in particular the considerable number of the lengthwise openings and/or the considerable number of the transverse openings, are at least partially cut out from an intermediate area of the sleeve, which is located between the catches and the flange. Because the openings are cut out in the intermediate area, a high pressing strength in the locked state is not compromised. In one area in which the catches are arranged, the sleeve has at least one radially closed wall of the sleeve over a large axial expansion area of the catches.

Except when the gripping edge is being locked, the syringe has a high tendency to burst in situations in which an internal pressure exceeds a bursting pressure in the barrel. Such an overshoot sometimes occurs in the case of mechanical injectors if the line power supply that powers the injectors fluctuates. Thus, a force that acts on a plug that is used as a plunger can be so large for a short time that a pressure that exceeds a bursting pressure of the barrel develops in the barrel. In such a case, the barrel bursts. Therefore, in an especially preferred further development of the invention, an independently inventive aspect is implemented, according to which it is provided that the flange is separated from the gripping edge if a boundary force is exceeded. It is preferably provided that a considerable number of break-away arms are made between the flange and the catches. The break-away arms are intended to ensure that when there is a preset force interval before the burst strength limit of the cylinder is reached, breaking takes place such that the connection between the flange and the sleeve is severed. As a result, the transfer of force from the injector to the syringe is interrupted.

In a preferred embodiment, it is consequently provided that the considerable number of break-away arms is configured such that the break-away arms break under the action of a force that lies below a bursting force, in which a bursting of the barrel takes place, in a specified force interval, such that the flange is detached from the catches. This embodiment is especially reliable since even before the bursting limit is reached, a separation of the flange from the remainder of the gripping edge is carried out. A risk of bursting during the injection of viscous liquids is thus reduced considerably. Undesirable drawbacks for medical personnel and/or patients by fragments that develop during bursting or a discharge of viscous liquid are avoided. Medical and technical processes are disrupted only to a slight extent or not at all, which results in cost savings.

The catches are preferably configured such that the assembly forces are reduced, the transmission of the forces during assembly is uniform, the deformation during assembly is minimized, and the catch is at maximum when subjected to a load (during injection) so that the gripping edge is not detached from the barrel.

Another independent inventive aspect to reduce the bursting tendency of a barrel is consequently produced in an embodiment of the invention in which the sleeve has a center axis and the large number of catches extend from the inside of the sleeve toward the inside to a center axis of the sleeve, such that in each case, a center area of the large number of catches has a smaller distance to the center axis than the edge areas of the catches. An inside edge of the catches that points to the center axis does not describe any concentric curve or surface relative to the center axis of the sleeve, which is a cylindrical axis in the case of a cylindrical basic shape of the sleeve. To this end, it is achieved that the forces that act on the catches (which are frequently designed as détentes) are reduced during locking. The forces no longer act as point forces. A deformation of the corners or the edge areas of the catches is reduced or completely avoided. Also, the forces that occur as point forces on the cylinder are reduced. Also, in the case of a circular groove, an improved attachment is achieved in addition to a reduction of the bursting tendency. Although in each case a contact surface of an abutting surface of the catches, which extends essentially at a right angle from an inside wall of the sleeve and is engaged in the locked state with the groove or the projection(s) of the barrel, is smaller with the groove or with the projection/projections than in the case of catches whose front edge presents a circular sector that is concentric to the cylindrical axis, the detaching forces, which are necessary to separate the gripping edge as a whole again from a barrel, increase. This is because during unlocking, the edge areas of the catches are no longer plastically deformed or are not so severely plastically deformed. Therefore, the abutting surfaces of the catches as a whole make better contact in the locked state. According to this aspect of the invention, the bursting tendency thus also decreases independently of the feature of the cut-out openings (which are cut out in particular as lengthwise openings and/or transverse openings).

An especially high breaking risk exists at the time in which the catches engage in one or more projections that are outside on the groove that goes around the barrel or behind one or more projections. At this time, the catches in most cases lock in a jerky manner. The force that is required for locking and that produces a deformation of the sleeve and hereby the catches in radial direction is exerted in axial direction to the gripping edge. To be able to intercept an axial movement that results from the locking and to reliably buffer the assembly forces that are generated at the time of the locking, preferably a considerable number of spring elements are made in the sleeve between the first opening and the second opening. Four spring elements are preferably provided. At the same time, the spring elements can be used as tension springs against the rotation of the gripping edge on the barrel.

In a preferred further development of the invention, the considerable number of spring elements are designed like leaf springs in a stop that projects radially toward the inside in the sleeve. For this purpose, the forces that occur when the gripping edge strikes the barrel can be buffered.

A stop that extends toward the inside also facilitates a specific positioning of the gripping edge. The gripping edge is preferably configured such that an outside proximal end of the barrel in the locked state adjoins the stop or rests on the stop. The latter also offers the possibility to "clamp" the barrel between the stop and the catches. A preferred embodiment of a gripping edge is distinguished in that the flange extends toward the inside from the sleeve to form the stop.

The spring elements are preferably configured such that the spring elements are essentially tapered from an edge area to the center. The action of a bundle of leaf springs thus can be emulated. In the center, the elasticity is at maximum. The spring elements, however, can also be configured in a different way. For example, the spring elements can be made to be flexible from the inside wall of the sleeve to the projections projecting toward the inside.

To ensure that an introduction of force into the spring elements is carried out in the center, it is advantageously provided that each of the spring elements comprises a projection that is used with the barrel as an interaction point.

The deformability of the spring elements in the area of the introduction of force is further increased in an embodiment in which the spring element has notches adjoining or adjacent to the projection to increase a deformability of the spring element adjoining the projection or adjacent to the projection.

To prevent a rolling of the syringe over a plane, it is provided in one embodiment that the flange has at least one cut-away section.

Polycarbonate is an economical material that makes possible a stable structure of the gripping edge; it therefore is advantageous if the gripping edge is produced from polycarbonate.

The description of one embodiment of the invention based on the figures follows. Here:

FIG. 6 shows a partial sectional view on the proximal end of the gripping edge according to FIG. 2;

FIG. 7 shows a sectional view of the gripping edge along the line B-B according to FIG. 6;

FIG. 8 shows a sectional view of the gripping edge along the line D-D according to FIG. 6;

FIG. 9 shows a cutaway of the gripping edge of the sectional view according to FIG. 7;

FIG. 11 shows a top view on the proximal end of the gripping edge;

FIG. 12 shows a sectional view of the gripping edge along the line E-E according to FIG. 11; and FIG. 13 shows a cutaway magnification of a spring element according to FIG. 12.

Figure 1:
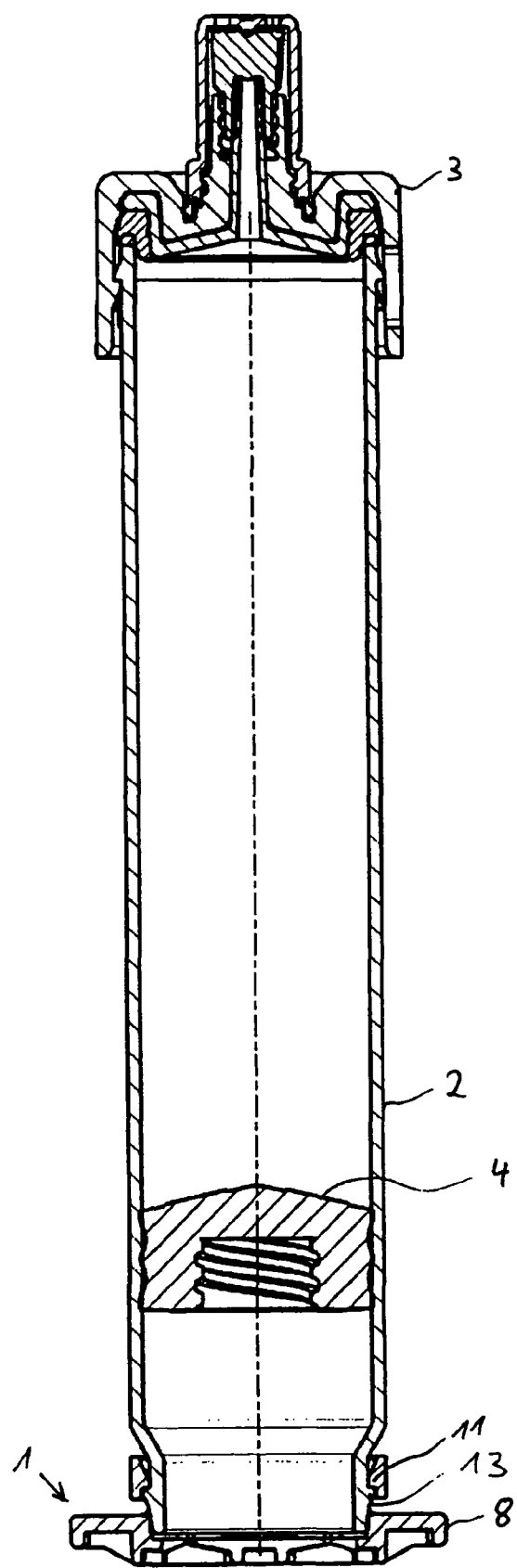
FIG. 1 shows a syringe with an attached gripping edge.

FIG. 1 shows a gripping edge 1 that is attached to a barrel 2. Stated more specifically, the gripping edge 1 is placed on the proximal end of the barrel 2, i.e., on the end that is facing the user. The distal end of the barrel is sealed by a cover cap 3. A plunger 4 is inserted into the barrel 2.

Figure 2:
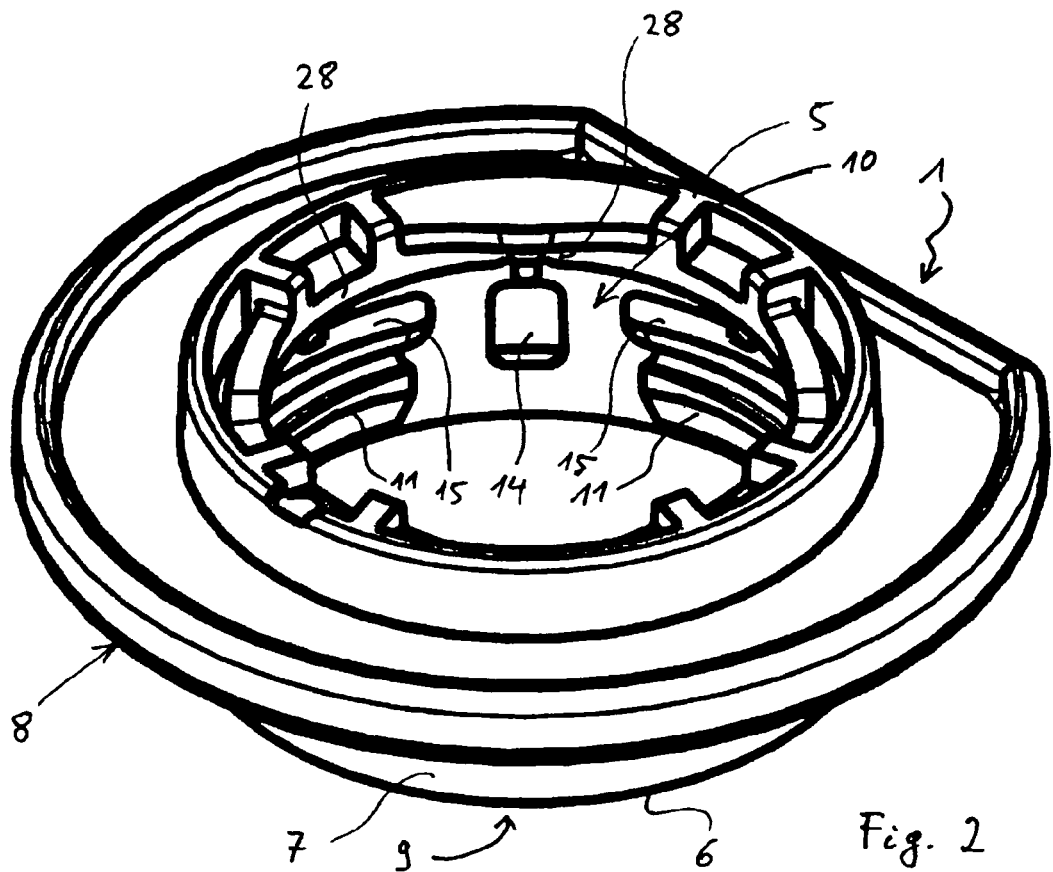
FIG. 2 shows a perspective view of the gripping edge according to one embodiment of the invention from below.
Figure 3:
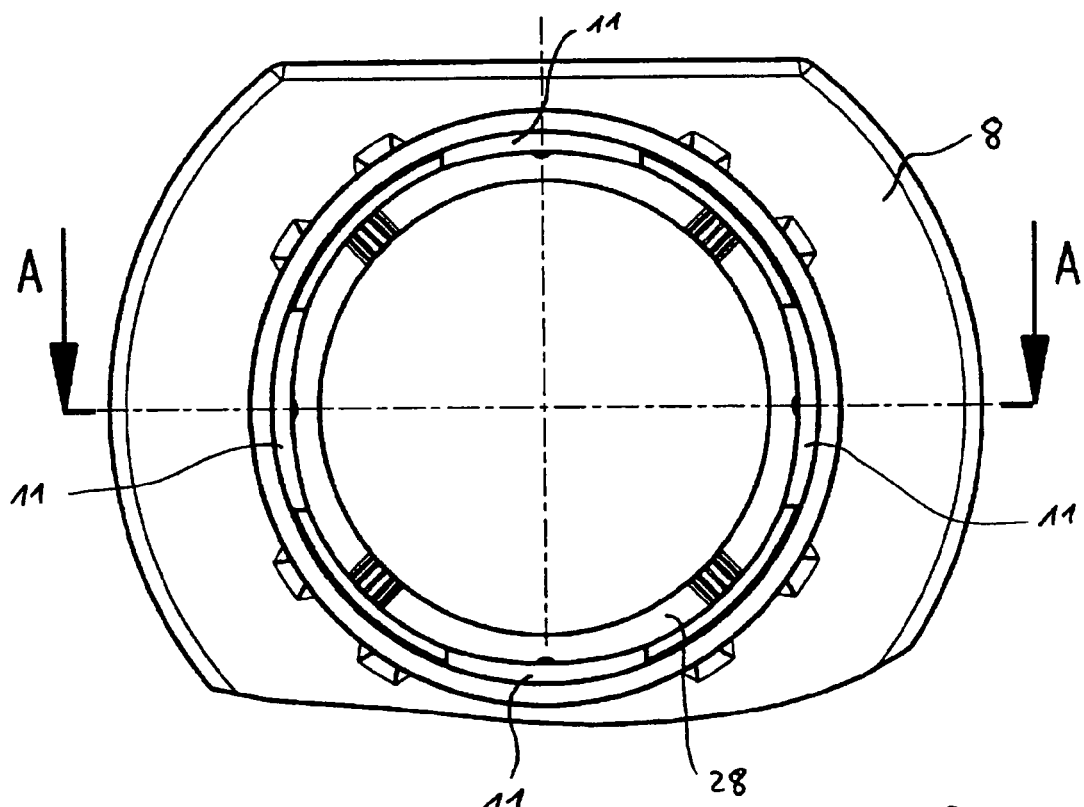
FIG. 3 shows a top view from the distal end on the gripping edge according to FIG. 2.
Figure 4:
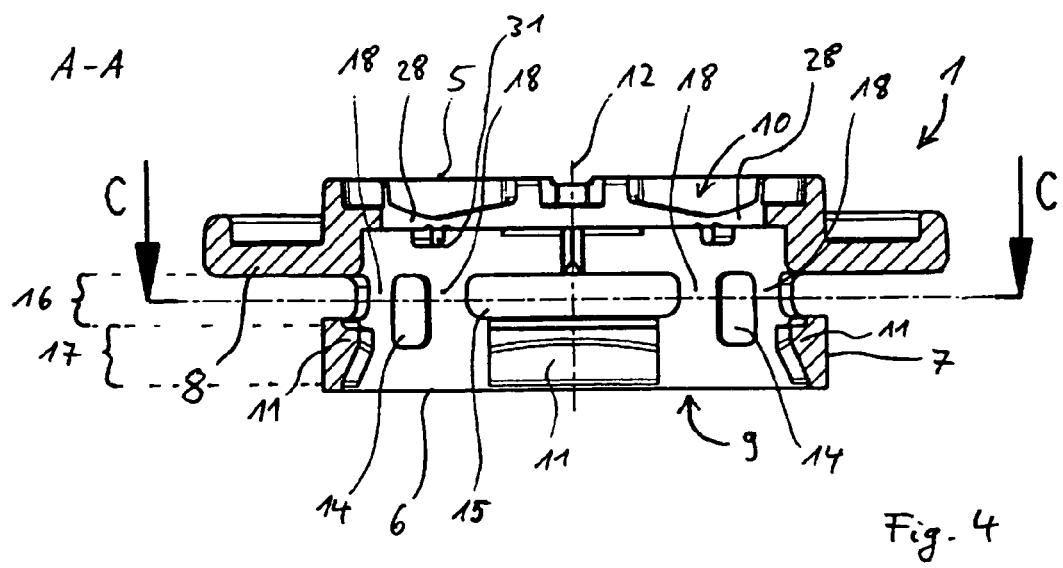
FIG. 4 shows a sectional view of the gripping edge according to the embodiment with expansion openings along line A-A according to FIG. 3.

FIG. 2 shows the gripping edge 1 from underneath, i.e., from the proximal end 5; FIG. 3 shows the gripping edge from above, i.e., a distal end 6 of the gripping edge in top view. FIG. 4 shows the gripping edge 1 in a section along the line A-A. As can be seen from FIG. 2, the gripping edge 1 has a sleeve 7 from which a flange 8 extends radially. The sleeve 7, as can be seen in particular in FIG. 4, has a first opening 9 that corresponds to the distal end 6 of the gripping edge 1. As can be seen from FIGS. 2 and 4, the flange is at a distance from the first opening 9 essentially at a second opening 10 that corresponds to the proximal end 5 of the gripping edge 1.

It can be seen from FIG. 2 that from the inside of the sleeve 7, catches 11 extend radially to the inside. The catches 11 that are designed as projections are shaped like "triangles" in cross-section, as can be seen from FIG. 4. On the distal end 6 of the sleeve 7, the catches 11 do not project from the inside wall of the sleeve; toward the proximal end 5, the catches 11 become thicker in one direction to a center axis 12 of the sleeve 7. As can be seen from FIG. 1, the catches 11, when the gripping edge 1 is placed on the barrel 2, grip behind projections 13 that are formed on the outside of the barrel 2 on the proximal end thereof. In this way, a more secure seat of the gripping edge 1 on the barrel 2 is produced.

As can be seen especially in FIGS. 2 and 4, in the wall of the sleeve 7, a large number of lengthwise openings 14 that extend in the axial direction of the sleeve 7 are formed; the embodiment is four lengthwise openings 14. In addition, in the wall of the sleeve 7, a large number of transverse openings 15 that extend peripherally in the wall of the sleeve 7 are formed. In the embodiment shown, there are four transverse openings 15. The lengthwise openings 14 and the transverse openings 15 allow the gripping edge to react elastically to the forces that occur. The lengthwise openings 14 and the transverse openings 15 are at least partially cut out from an intermediate area 16 of the sleeve 7. The area of the sleeve that is located in axial direction or lengthwise direction of the sleeve between the catches 11 and the flange 8 is referred to as intermediate area 16. The transverse openings 15 are cut out completely from the intermediate area 16. The lengthwise openings 14 are for the most part also cut out from the intermediate area 16. The lengthwise openings, however, project partially into a thus mentioned catch area 17, in which the catches 11 are molded to the sleeve 7. In a direction parallel to the center axis 12, however, the catch area 17 is formed without openings in a large area closed around an entire periphery of the sleeve 7. As a result, it is achieved that the catch, when the gripping edge 1 is fastened to the barrel 2, remains securely engaged with the projection or the projections 13 of the barrel. The distal end 6 does not have any openings in the sleeve 7.

Figure 5:
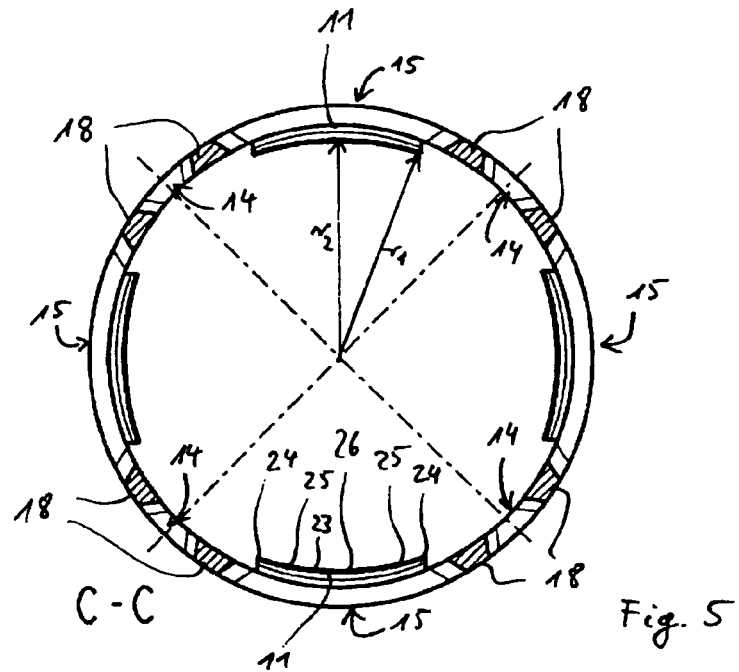
FIG. 5 shows a sectional view of the gripping edge along the line C-C according to FIG. 4.

FIG. 5 shows a sectional view of the gripping edge 1 along the line C-C in FIG. 4. It can be seen in particular in FIG. 5 that a large number of break-away arms 18 are formed. The break-away arms 18 are produced by especially thinly formed arms between the lengthwise openings 14 and the transverse openings 15. The break-away arms 18 make it possible to separate the flange 8 from the sleeve 7 in case of emergency.

As can be seen in particular from FIG. 5, the large number of catches 11 in this embodiment is four. The catches 11 are formed by the "tip" edges that point toward the inside.

In FIG. 6, a top view on the proximal end 5 of the gripping edge is shown. The related sectional views along lines B-B and D-D are depicted accordingly in FIG. 7 and FIG. 8. A cutout X of FIG. 7 is shown in FIG. 9.

As can be seen in particular from FIGS. 7 to 9, the catches 11 have a greatly simplified triangular shape. Therefore, the catches have an inclined surface 19 and an abutting surface 20 that extends essentially at a right angle away from the sleeve 7. The inclined surface 19 runs to the distal end 6 of the sleeve 7 at an acute angle to an inside wall 21 of the sleeve 7 and becomes rounded off in the latter.

The abutting surface 20 that extends essentially at a right angle from the sleeve 7 also becomes rounded off in the inside wall 21 of the sleeve 7. Both the inclined surface 19 and the abutting surface 20 can turn into other embodiments with an acute angle or essentially into a right angle in the inside wall 21.

Figure 10:
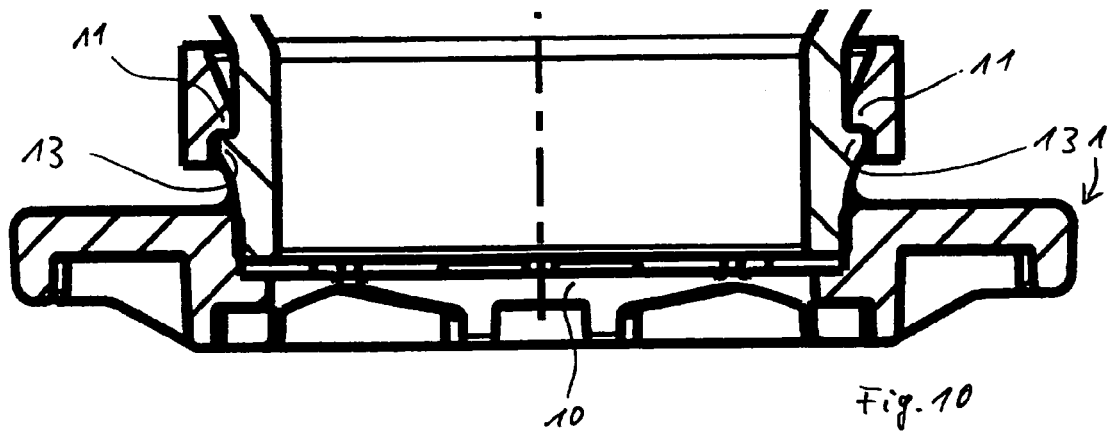
FIG. 10 shows a detail view of the proximal end of the barrel with the attached gripping edge from FIG. 1.

If the gripping edge 1 is pushed onto the proximal end of the barrel 2, the catches 11 of the gripping edge 1 lock behind the projections 13 of the barrel 2, as the latter can readily be seen in FIG. 10, which shows a cutaway magnification of the proximal end of the barrel 2 with the locked gripping edge 1. The gripping edge 1 is therefore easily pushed onto the barrel 2, but it cannot be pulled down again.

As can readily be seen especially from FIGS. 7 to 10, a support surface 22 that runs essentially perpendicular to a plane that is formed by the distal opening 6 is formed on the catches 11 between the inclined surface 19 and the abutting surface 20 that essentially extends at a right angle from the sleeve. This provides for the fact that a front edge 23 of the abutting surface 20 that extends essentially at a right angle from the sleeve is damaged neither during locking nor in the case of an action of force along a detaching device.

If this edge 23 is damaged, the abutting surface 20 does not lie flat on the projection or projections 13 of the barrel 2. This results in a reduction of the detaching forces that are necessary to further remove the gripping edge 1 from the barrel 2.

When a gripping edge is locked on a barrel, in which the front edge and/or support surfaces of the catches are designed in each case as concentric circular segments or cylindrical sector elements in a center axis of the sleeve, significantly greater forces than in a center area act on edges or edge areas of the catches. This drawback is eliminated in the embodiment described here. In the embodiment described, corners 24 and edge areas 25 of the catches 11 have a larger distance $r_1$ from the center axis 12 of the sleeve 7 than a center area 26. A distance $r_2$ from the center axis 12 of the sleeve 7 to the center area 26 of the catch 11 is thus greater than the distance $r_1$. In this respect, especially plastic deformations of edges 24 are avoided or reduced during locking. To this end, the abutting surface 20 is smaller compared to the "concentric" variant of the catches by the improved adjoining to the projection or projections 13 in the locked state since an improved resistance against a detaching of the gripping edge 1 is achieved.

As can be seen in particular in FIGS. 2, 3, 7 and 10, a stop 27 that projects toward the inside from the inside wall 21 is formed. The gripping edge 1 can be pushed onto the proximal end of the barrel 2 until the stop 27 pushes against an outside proximal end of the barrel 2. Thus, a specific positioning of the gripping edge 1 is possible.

The force that is required for locking acts on the gripping edge 1 that is essentially parallel to the center axis 12 to produce a radial deformation of the sleeve 7 and/or the catches 11. At the time in which the catches 11 are locked behind the projection or the projections 13, the energy that is stored in the deformed sleeve and/or the deformed catches 11 is free. Also, the force generally acts with an axial action. As a result, when the stop 27 strikes the proximal end of the barrel, an impact force is exerted on the latter. To be able to intercept this impact force, spring elements 28 are placed in the stop 27. The latter can be seen most advantageously in FIG. 12 and FIG. 13, a cutout magnification Z of FIG. 12. FIG. 12 shows a sectional view along a line E-E of FIG. 11, which again shows essentially the same view of the gripping edge 1 as FIG. 6.

In the stop 27, four spring elements 28 are formed. The spring elements 28 are similar in their design to leaf springs, which are curved concentrically to the center axis 12.

Thickness of the spring elements 28 is tapered from the edge areas 29 in each case to the center 30. In the center 30, in each case a projection 31 that projects to the distal end 6 of the sleeve 7 is formed. The latter acts as an interaction point or surface with the barrel.

As a result, an introduction of a force in the middle into the spring elements 28 is achieved.

To obtain flexibility near the center 30 of the spring elements despite the projections 31, in each case notches 32 are made adjacent to the projection 31.

In the locked stage, the projections 31 advantageously adjoin the outside proximal end of the barrel 2 or are engaged with the latter. Especially preferably, the spring elements 28 in the locked state are even slightly tensioned. As a result, a twisting of the gripping edge 1 relative to the barrel 2 can be prevented.

As can be seen especially from FIGS. 2, 3, 6 and 11, the flange 8 is not shaped to be completely circular. Rather, a segment is cut away so that a straight section 33 is formed that prevents rolling if the syringe is laid down on a flat surface.

The gripping edge 1 is made preferably from polycarbonate. Polycarbonate can be easily sterilized, but has sufficient strength so that the gripping edge 1 can protect the proximal end of the barrel 2 even from mechanical damage.

LEGEND

1 Gripping edge
2 Barrel
3 Cover cap
4 Plunger
5 Proximal end of the gripping edge
6 Distal end of the gripping edge
7 Sleeve
8 Flange
9 First opening
10 Second opening
11 Catches on the inside of the sleeve
12 Center axis of the sleeve
13 Projections on the barrel
14 Lengthwise openings in the axial direction
15 Transverse openings in the peripheral direction
16 Intermediate area
17 Catch area
18 Break-away arm
19 Inclined surface
20 Abutting surface
21 Inside wall of the sleeve
22 Support surfaces
23 Front edge of the catches
24 Corners of the catch
25 Edge areas of the catch
26 Center area of the catch
27 Stop
28 Spring elements
29 Edge area of the spring element
30 Middle of the spring element
31 Projection
32 Notch
33 Straight section Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 102005042076.1, filed Aug. 31, 2005, and U.S. Provisional Application Ser. No. 60/713,758, filed Sep. 6, 2005, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A gripping edge (1) for a syringe, said gripping edge comprising:
    a sleeve (7) with a first opening (9) for slipping onto the exterior surface of a barrel (2) of a syringe and a second opening (10), said sleeve having an inside wall (21);
    a flange (8) that is attached to said sleeve (7) that faces away from said first opening (9);
    a plurality of catches (11) that project radially inward from said inside wall (21) of said sleeve (7);
    a plurality of lengthwise openings (14) and a plurality of transverse openings (15) provided in said sleeve (7), wherein said lengthwise and transverse openings do not extend to said first opening (9); and
    a plurality of break-away arms (18) positioned between said flange (8) and said catches (11), and wherein each of said break-away arms (18) is located between one of said lengthwise openings (14) and one of said transverse openings (15).

2. A gripping edge (1) according to claim 1, wherein said plurality of lengthwise openings and plurality of transverse openings are cut out at least partially from an intermediate area (16) of said sleeve (7), which is located between said catches (11) and said flange (8).

3. A gripping edge (1) according to claim 1, wherein said plurality of break-away arms (18) are configured such that the break-away arms (18) break off in the case of an action of force, which is below a bursting force in a specified force interval, in which a bursting of the barrel (2) occurs, whereby said flange (8) is separated from said catches (11).

4. A gripping edge (1) according to claim 1, wherein said sleeve (7) has a center axis (12), said plurality of catches (11) extend radially inward from said inside wall (21) of said sleeve (7) towards said to center axis (12) of said sleeve (7), each of said plurality of catches having a center area (26) and edge areas (25), and said center area (26) of each of said catches (11) is positioned a shorter distance from said center axis (12) than said edge areas (25).

5. A gripping edge (1) according to claim 1, further comprising a plurality of spring elements (28) formed in said sleeve (7) between said first opening (9) and said second opening (10).

6. A gripping edge (1) according to claim 5, wherein said plurality of spring elements (28) are in the form of leaf springs in a stop (27) that projects radially inward within said sleeve (7).

7. A gripping edge (1) according to claim 5, wherein each of said spring elements (28) are tapered from edge areas (29) to their middle (30).

8. A gripping edge (1) according to claim 5, wherein each of said spring elements (28) comprises a projection (31) that is used as an interaction point with a barrel (2) of a syringe.

9. A gripping edge (1) according to claim 8, wherein said spring element (28) has notches (32) adjoining or adjacent to said projection (31) to increase deformability of said spring element (28).

10. A gripping edge (1) according to claim 6, wherein said stop (27) is positioned within said sleeve (7) between second opening (10) and an intermediate area (16) of said sleeve (7), said intermediate area (16) being located between said catches (11) and said flange (8).

11. A gripping edge (1) according to claim 1, wherein said flange (8) has at least one straight section (33) to prevent rolling.

12. A gripping edge (1) according to claim 1, wherein said gripping edge is made of polycarbonate.

13. A gripping edge (1) according to claim 1, wherein said catches (11) have a triangular cross-section.

14. A gripping edge (1) according to claim 2, wherein said transverse openings (15) are cut out completely from said intermediate area (16).

15. A gripping edge (1) according to claim 2, wherein said plurality of lengthwise openings (14) are partially cut out from said intermediate area (16), and said plurality of lengthwise openings (14) extend partially into a catch area (17), in which the catches (11) project radially inward from said inside wall (21) of said sleeve (7).

16. A gripping edge (1) according to claim 14, wherein said plurality of lengthwise openings (14) are partially cut out from said intermediate area (16), and said plurality of lengthwise openings (14) extend partially into a catch area (17), in which the catches (11) project radially inward from said inside wall (21) of said sleeve (7).

17. A gripping edge (1) according to claim 1, wherein each of said catches comprises an inclined surface (19) which inclines upwards towards said second opening (10), and an abutting surface (20) that extends essentially at a right angle away from said sleeve (7).

18. A gripping edge (1) according to claim 17, wherein each of said catches further comprises a support surface (22), that is essentially perpendicular to a plane formed by said first opening (9), wherein said support surface (22) is formed between said inclined surface (19) and said abutting surface (20).

19. A syringe with attached gripping edge comprising:
a syringe having a barrel (2) and projections 13 formed on the outside of said barrel (2) at a proximal end thereof; and
a gripping edge according to claim 1 positioned on the exterior of said syringe.

20. A gripping edge (1) according to claim 1, wherein said plurality of catches (11) project radially inward from said inside wall (21) of said sleeve (7) and are inclined upwards from said inside wall (21) towards said second opening (10).

21. A gripping edge (1) according to claim 1, wherein each of said plurality of transverse openings is positioned above a catch (11) in an intermediate area (16) of said sleeve (7), which is located between said catches (11) and said flange (8).

22. A gripping edge (1) according to claim 1, wherein said break-away arms do not project radially inward from said inside wall (21).

23. A gripping edge (1) according to claim 5, wherein each of said spring elements are positioned in an intermediate area (16) of said sleeve (7), which is located between said catches (11) and said flange (8).

* * * * *